(12) United States Patent
Starkley

(10) Patent No.: US 10,357,031 B1
(45) Date of Patent: Jul. 23, 2019

(54) INSECT REPELLING RECYCLED FIRE LOG

(71) Applicant: Michael Starkley, Brooklyn, NY (US)

(72) Inventor: Michael Starkley, Brooklyn, NY (US)

( * ) Notice: Subject to any disclaimer, the term of this patent is extended or adjusted under 35 U.S.C. 154(b) by 140 days.

(21) Appl. No.: 15/358,204

(22) Filed: Nov. 22, 2016

(51) Int. Cl.
| | | |
|---|---|---|
| *A01N 25/02* | (2006.01) | |
| *A01N 25/20* | (2006.01) | |
| *A01N 31/00* | (2006.01) | |
| *A01N 33/00* | (2006.01) | |
| *A01N 43/653* | (2006.01) | |
| *A01P 3/00* | (2006.01) | |
| *A62B 23/00* | (2006.01) | |
| *A62B 7/10* | (2006.01) | |

(Continued)

(52) U.S. Cl.
CPC ............. *A01N 25/20* (2013.01); *A01N 25/08* (2013.01); *A01N 65/06* (2013.01); *A01N 65/22* (2013.01); *C10L 5/146* (2013.01); *C10L 5/442* (2013.01); *C10L 2200/0469* (2013.01); *C10L 2230/06* (2013.01)

(58) Field of Classification Search
CPC . Y02E 50/10; Y02E 50/30; C10L 5/44; C10L 5/442; C10L 5/363; C10L 5/445; C10L 2200/0469; C10L 2290/08; C10L 2290/30; C10L 5/08; C10L 5/12; C10L 5/14; C10L 5/146; C10L 5/361; C10L 5/403; C10L 5/406; C10L 5/20; C10L 5/365; C10L 5/34; A01K 1/0154; A01K 1/0155; B01J 20/20; B01J 20/24; B01J 20/261; B01J 20/262; B01J 20/2803; B01J 20/28042; B01J 20/3035; B01J 20/3042; B01J 2220/44; B01J 2220/46; B01J 2220/4831; B01J 2220/485; B01J 2220/4887; B01J 2220/68; A01M 1/2066; A01M 29/12; A01M 31/008; A23B 4/044; A61L 9/046; A61L 9/12; C03B 5/26; C03B 7/02; C03B 7/06; C03B 7/08; C03B 7/088; A01N 25/02; A01N 31/00; A01N 31/14; A01N 33/00; A01N 33/04; A01N 43/653; A01P 3/00; A41D 13/11; A42B 1/18; A62B 23/00; A62B 7/10; B27K 3/16; B27K 3/34; B27K 3/38; B65D 69/00; F21S 15/00; F21V 21/12; F24B 1/195

See application file for complete search history.

(56) References Cited

U.S. PATENT DOCUMENTS

| 3,880,611 A | 4/1975 | Weiss | |
|---|---|---|---|
| 3,894,848 A * | 7/1975 | Kleiman | C10L 5/40 44/628 |

(Continued)

FOREIGN PATENT DOCUMENTS

WO   2014158409 A1   10/2014

*Primary Examiner* — Ellen M McAvoy
*Assistant Examiner* — Chantel L Graham
(74) *Attorney, Agent, or Firm* — Kyle A. Fletcher, Esq.

(57) ABSTRACT

The insect repelling recycled fire log is a manufactured fuel product that is configured for use as a fuel in a recreational combustion activity such as a bonfire or a campfire. The insect repelling recycled fire log releases an insect repellent that encourages insects to move away from the immediate areas surrounding the recreational combustion activity area during the said activities. The natural insect repellent is an airborne repellent that is released by the combustion of the insect repelling recycled fire log. The insect repelling recycled fire log comprises a fuel, an accelerant, and an ignition apparatus.

14 Claims, 2 Drawing Sheets

(51) Int. Cl.
*B27K 3/15* (2006.01)
*C10L 5/34* (2006.01)
*F21S 15/00* (2006.01)
*A01N 25/08* (2006.01)
*A01N 65/06* (2009.01)
*A01N 65/22* (2009.01)
*C10L 5/44* (2006.01)
*C10L 5/14* (2006.01)

(56) References Cited

U.S. PATENT DOCUMENTS

| | | | | |
|---|---|---|---|---|
| 4,308,033 | A | * | 12/1981 | Gunnerman ............. C10L 5/44 44/530 |
| 4,941,889 | A | * | 7/1990 | Holmes ................. A23B 4/044 44/545 |
| D362,655 | S | | 9/1995 | Bain |
| 5,496,384 | A | | 3/1996 | Jeskey |
| 6,419,898 | B1 | | 7/2002 | Flashinski |
| 6,660,051 | B2 | | 12/2003 | Chandaria |
| 7,399,324 | B2 | * | 7/2008 | Roddenbery ....... A01M 1/2066 44/530 |
| 8,636,816 | B1 | * | 1/2014 | Svopa, Jr. ............... C10L 5/445 44/578 |
| 2002/0129808 | A1 | * | 9/2002 | Manner .................... C10L 5/40 126/45 |
| 2003/0175369 | A1 | * | 9/2003 | Khazan-Enache ..... A01N 65/00 424/739 |
| 2004/0045215 | A1 | * | 3/2004 | Guilfoyle ................. C10L 5/44 44/577 |
| 2006/0117649 | A1 | * | 6/2006 | Schweickhardt ........ C10L 5/36 44/535 |
| 2010/0300368 | A1 | * | 12/2010 | Myers .................. A01K 1/0154 119/171 |
| 2013/0067805 | A1 | * | 3/2013 | Geffen .................... C10L 5/363 44/589 |
| 2014/0157660 | A1 | * | 6/2014 | Carrera Varela ........ C10L 5/363 44/589 |
| 2016/0158121 | A1 | * | 6/2016 | Lei ........................ C11D 3/505 424/401 |

* cited by examiner

INSECT REPELLING RECYCLED FIRE LOG

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of chemistry including fuels, more specifically, a solid fuel further configured for use as an insect repellent.

SUMMARY OF INVENTION

The insect repelling recycled fire log is a manufactured fuel product that is configured for use as a fuel in a recreational combustion activity such as a bonfire or a campfire. The insect repelling recycled fire log releases an insect repellent that encourages insects to move away from the immediate areas surrounding the recreational combustion activity area during the said activities. The natural insect repellent is an airborne repellent that is released by the combustion of the insect repelling recycled fire log. The insect repelling recycled fire log comprises a fuel, an accelerant, and an ignition apparatus.

These together with additional objects, features and advantages of the insect repelling recycled fire log will be readily apparent to those of ordinary skill in the art upon reading the following detailed description of the presently preferred, but nonetheless illustrative, embodiments when taken in conjunction with the accompanying drawings.

In this respect, before explaining the current embodiments of the insect repelling recycled fire log in detail, it is to be understood that the insect repelling recycled fire log is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the insect repelling recycled fire log.

It is therefore important that the claims be regarded as including such equivalent construction insofar as they do not depart from the spirit and scope of the insect repelling recycled fire log. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
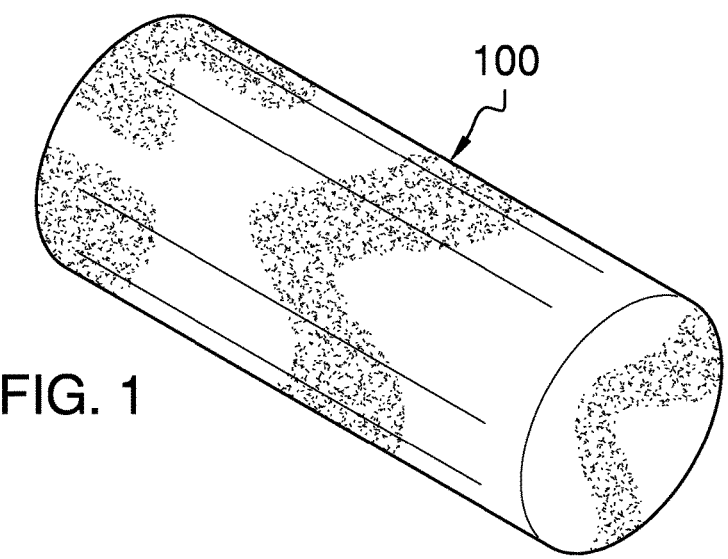
FIG. 1 is a perspective view of an embodiment of the disclosure.
Figure 2:
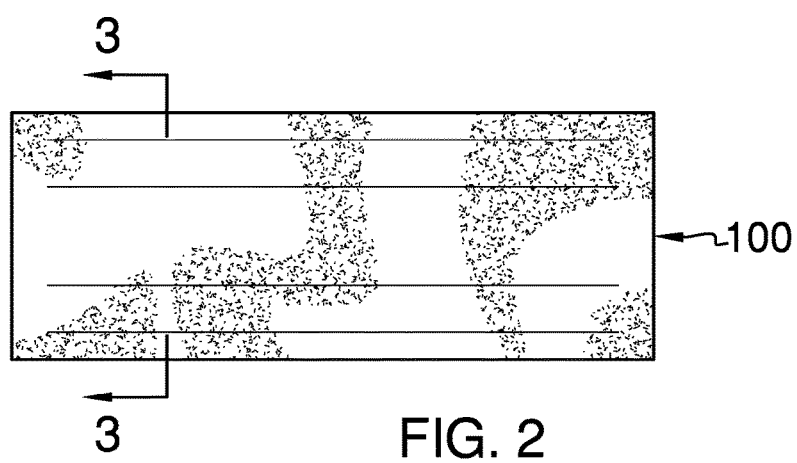
FIG. 2 is a side view of an embodiment of the disclosure.
Figure 3:
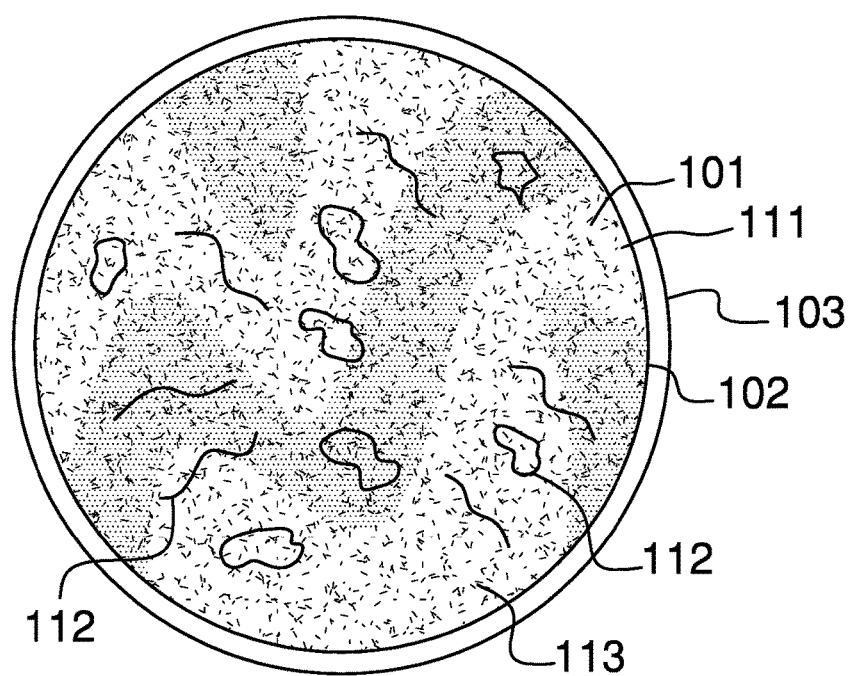
FIG. 3 is a cross-sectional view of an embodiment of the disclosure across 3-3 as shown in FIG. 2.

Detailed reference will now be made to one or more potential embodiments of the disclosure, which are illustrated in FIGS. 1 through 3.

The insect repelling recycled fire log 100 (hereinafter invention) comprises a fuel 101, an accelerant 102, and an ignition apparatus 103. The fuel 101 and the accelerant 102 form a mixture that is compressed into a solid form. The solid form is covered within an ignition apparatus 103. The ignition apparatus 103 is formed from a readily and commercially available combustible paper product that, once ignited, ignites the accelerant 102, which causes the invention 100 to burn. The invention 100 is a manufactured fuel 101 product that is configured for use as a fuel 101 in a recreational combustion activity such as a bonfire or a campfire. The invention 100 releases an insect repellent that encourages insects to move away from the immediate areas surrounding the recreational combustion activity area during the said activities. The natural insect repellent is an airborne repellent that is released by the combustion of the invention 100.

In the first potential embodiment of the disclosure, the fuel 101 consists of a mixture of sawdust 111 and a repellent source 112. The repellent source 112 consists of solid biological material that releases a natural insect repellent when burned. The accelerant 102 consists of paraffin 113. The paraffin 113 forms a binder that binds the sawdust 111, the repellent source 112, and the paraffin 113 as a solid object during combustion. The proportion of the mass of the fuel 101 ranges between 67% and 75% (m/m inclusive) of the combined masses of the fuel 101 and the accelerant 102. The proportion of the mass of the repellent source 112 to the sum of the mass of the fuel 101 and the mass of the accelerant 102 ranges between 17% and 30% (m/m inclusive).

In a second potential embodiment of the disclosure, the repellent source 112 consists of readily and commercially available cedar chips.

In a third potential embodiment of the disclosure, the repellent source 112 consists of readily and commercially available dried sage.

In a fourth potential embodiment of the disclosure, the repellent source 112 consists of a mixture of readily and commercially available cedar chips and readily and commercially available dried sage.

In the fifth potential embodiment of the disclosure, the fuel 101 consists of sawdust 111. The accelerant 102 consists of a mixture of paraffin 113 and a repellent source 112. The repellent source 112 consists of an essential oil derived from biological matter that contains a natural insect repellent. The accelerant 102 forms a binder that holds the sawdust 111, the repellent source 112, and the paraffin 113 as a solid object during combustion. The proportion of the mass of the accelerant 102 ranges between 3% and 7% (m/m inclusive) of the combined mass of the fuel 101 and the accelerant 102. The proportion of the mass of the repellent source 112 to the total mass of the accelerant 102 ranges between 22% and 50% (m/m inclusive).

In a sixth potential embodiment of the disclosure, the repellent source 112 consists of a readily and commercially essential oil derived from cedar.

In a seventh potential embodiment of the disclosure, the repellent source 112 consists of a readily and commercially available essential oil derived from sage.

In an eighth potential embodiment of the disclosure, the repellent source 112 consists of a mixture of a readily and commercially essential oil derived from cedar and a readily and commercially available essential oil derived from sage.

The following definitions were used in this disclosure:

Accelerant: As used in this disclosure, an accelerant is a chemical that speeds up the chemical reaction of combustion.

Cedar: As used in this disclosure, cedar refers to the plant botanically known as *cedrela odorata*.

Cedar Chips: As used in this disclosure, the term cedar chips refers to dried nuggets and particles derived from the cedar plant.

Essential Oil: As used in this disclosure, an essential oil is a lipid-based solution that contains one or more volatile aroma compounds.

Paraffin: As used in this disclosure, paraffin is an alkane with a carbon base chain of between 20 and 40 atoms that is solid at room temperature.

Sage: As used in this disclosure, sage refers to the plant botanically known as *salvia officinalus*.

Sawdust: As used in this disclosure, sawdust is a powder formed from particulates of wood that has been sawn or otherwise chipped.

With respect to the above description, it is to be realized that the optimum dimensional relationship for the various components of the invention described above and in FIGS. 1 through 3 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A combustion device comprising:
   a fuel, an accelerant, and an ignition apparatus;
   wherein the fuel and the accelerant form a mixture that is compressed into a solid form;
   wherein the solid form is covered within an ignition apparatus;
   wherein the ignition apparatus ignites the accelerant;
   wherein the combustible device releases an insect repellent during combustion;
   wherein the fuel is a mixture of sawdust and a repellent source;
   wherein the repellent source consists of solid biological material that releases the insect repellent when burned;
   wherein the accelerant is a paraffin that binds the sawdust, the repellent source, and the paraffin into a solid object during combustion;
   wherein the proportion of the mass of the fuel ranges between 67% and 75% (m/m inclusive) of the combined masses of the fuel and the accelerant;
   wherein the proportion of the mass of the repellent source to the sum of the mass of the fuel and the mass of the accelerant ranges between 17% and 30% (m/m inclusive).

2. The combustion device according to claim 1 wherein the repellent source consists of cedar chips.

3. The combustion device according to claim 1 wherein the repellent source consists of dried sage.

4. The combustion device according to claim 1 wherein the repellent source consists of a mixture of cedar chips and dried sage.

5. The combustion device according to claim 1
   wherein the repellent source consists of an essential oil derived from biological matter;
   wherein the repellent source contains a natural insect repellent.

6. The combustion device according to claim 5 wherein the proportion of the mass of the accelerant to the ranges between 3% and 7% (m/m inclusive) of the combined mass of the fuel and the accelerant.

7. The combustion device according to claim 6 wherein the proportion of the mass of the repellent source to the total mass of the accelerant ranges between 22% and 50% (m/m inclusive).

8. The combustion device according to claim 7 wherein the repellent source consists of an essential oil derived from cedar.

9. The combustion device according to claim 7 wherein the repellent source consists of an essential oil derived from sage.

10. The combustion device according to claim 7 wherein the repellent source consists of a mixture of a first essential oil derived from cedar and a second oil derived from sage.

11. A combustion device comprising:
    a fuel, an accelerant, and an ignition apparatus;
    wherein the fuel and the accelerant form a mixture that is compressed into a solid form;
    wherein the solid form is covered within an ignition apparatus;
    wherein the ignition apparatus ignites the accelerant;
    wherein the combustible device releases an insect repellent during combustion;
    wherein the fuel comprises a mixture of sawdust and a repellent source;
    wherein the repellent source comprises a solid biological material that releases the insect repellent when burned;
    wherein the accelerant comprises paraffin;

wherein the paraffin binds the sawdust, the repellent source, and the paraffin into a solid object during combustion;

wherein the proportion of the mass of the of fuel ranges between 67% and 75% (m/m inclusive) of the combined masses of the fuel and the accelerant;

wherein the proportion of the mass of the repellent source to the sum of the mass of the fuel and the mass of the accelerant ranges between 17% and 30% (m/m inclusive);

wherein the repellent source comprises cedar chips;

wherein the repellent source further comprises dried sage;

wherein the fuel comprises sawdust;

wherein the accelerant comprises a mixture of paraffin and a repellent source;

wherein the repellent source comprises an essential oil derived from biological matter;

wherein the repellent source contains a natural insect repellent;

wherein the accelerant forms a binder that holds the sawdust, the repellent source, and the paraffin as a solid object during combustion;

wherein the proportion of the mass of the accelerant to the ranges between 3% and 7% (m/m inclusive) of the combined mass of the fuel and the accelerant;

wherein the proportion of the mass of the repellent source to the total mass of the accelerant ranges between 22% and 50% (m/m inclusive).

12. The combustion device according to claim 11 wherein the repellent source comprises an essential oil derived from cedar.

13. The combustion device according to claim 12 wherein the repellent source comprises an essential oil derived from sage.

14. The combustion device according to claim 13 wherein the repellent source comprises a mixture of a first essential oil derived from cedar and a second oil derived from sage.

\* \* \* \* \*